US006251445B1

(12) United States Patent
Han et al.

(10) Patent No.: US 6,251,445 B1
(45) Date of Patent: *Jun. 26, 2001

(54) METHOD FOR PRODUCING ENZYME-MODIFIED CHEESE FLAVORINGS

(75) Inventors: Xiao-Qing Han, Naperville; Richard S. Silver, Wilmette; Peter H. Brown, Glenview, all of IL (US)

(73) Assignee: Kraft Foods, Inc., Northfield, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,713

(22) Filed: May 19, 1999

(51) Int. Cl.$^7$ ........................................... A23C 9/12
(52) U.S. Cl. .................. 426/36; 426/41; 426/43
(58) Field of Search .................. 426/35, 36, 41, 426/42, 43, 534, 650, 582, 583; 435/68.1

(56) References Cited

U.S. PATENT DOCUMENTS

| | | |
|---|---|---|
| 3,535,304 | 10/1970 | Muller et al. . |
| 4,113,895 | 9/1978 | Watt et al. ............................. 427/44 |
| 4,205,090 | 5/1980 | Maubois et al. . |
| 4,500,549 * | 2/1985 | Crossman ............................ 426/33 |
| 4,595,594 | 6/1986 | Lee et al. ............................. 426/35 |
| 4,675,193 * | 6/1987 | Boudreaux ........................... 426/35 |
| 4,752,483 | 6/1988 | Hagberg et al. ..................... 426/35 |
| 5,156,956 | 10/1992 | Motoki et al. . |
| 5,211,972 | 5/1993 | Kratky et al. ....................... 426/35 |
| 5,356,639 | 10/1994 | Jameson et al. . |
| 5,523,237 | 6/1996 | Budtz et al. . |
| 5,681,598 | 10/1997 | Kuraishi et al. . |
| 5,731,183 | 3/1998 | Kobayashi et al. . |

FOREIGN PATENT DOCUMENTS

| | | |
|---|---|---|
| 59059151 | 4/1984 | (JP) . |
| 02276541 | 11/1990 | (JP) . |
| 93/22930 | 11/1993 | (WO) . |
| 94/21129 | 9/1994 | (WO) . |
| 94/21130 | 9/1994 | (WO) . |
| 97/01961 | 1/1997 | (WO) . |

OTHER PUBLICATIONS

Ernstrom et al., J. Dairy Science 63:228–234 (1980).
Banks, J.M. et al., IG [1987]. Increasing the yield of Cheddar Cheese by the acidification of milk containing heat denatured whey protein. Milchwissenschaft 42 (4), pp. 212–215.
Law, A.J.R. et al., IG [1994]. Denaturation of the whey proteins in heat milk and their incorporation into Cheddar cheese. Milchwissenschaft 49 (2), pp. 63–67.
Guinee, Timothy P. et al., Composition, Microstructure and Maturation of Semi–Hard Cheeses From High Protein Ultra–filtered Milk Retentates With Different Levels of Denatured Whey Protein, Int. Dairy Journal 5, p. 543–568.
Han, Xiao–Qing et al., [1996]. Thermodynamic Compatibility of Substrate Proteins Affects of Their Cross–Linking By Transglutaminase. J. Agri. Food Chem. 44 (5) pp. 1211–1217.
Dybing S. T., et al. [1998] , Dairy Foods— The Ability of Phosphates or — Carrageenan to Coagulate Whey Proteins and the Possible Uses of Such Coagula in Cheese Manufacture. J. Dairy Sci. 81 (2) pp. 309–317.
Dalgleish, D. G., et al., [1997] Heat–Induced Interactions of Whey Proteins and Casein Micelles with Different Concentrations of $\alpha$–Lactalbumin and $\beta$–Lactoglobulin, J. Agric. Food. Chem., 45, pp. 4806–4813.
Dalgleish, D. G., et al. [1997] Interactions between $\alpha$–Lactalbumin and $\beta$–Lactoglobulin in the Early Stages of Heat Denaturation, J. Agric Food Chem. 45 pp. 3459–3464.
Noh, B., et al. [1989] Incorporation of Radiolabeled Whey Proteins into Casein Micelles by Heat Processing, J. Dairy Sci. 72 pp. 1724–1731.
Noh, B., et al. [1989] Radiolabelling Study of Heat–induced Interactions Between $\alpha$–Lactalbumin, $\beta$–Lactoglobulin and $\kappa$–Casein in Milk and in Butter Solutions, Journal of Food Science, vol. 54, No. 4, pp. 889–893.
Kosikowski, Cheese and Fermented Foods, $2^{nd}$ ed., Edward Brothers, Inc., Ann Arbor, MI, 1977, pp. 451–458.

* cited by examiner

*Primary Examiner*—Keith Hendricks
(74) *Attorney, Agent, or Firm*—Fitch, Even, Tabin & Flannery

(57) ABSTRACT

The present invention provides a process for making an enzyme-modified cheese flavoring in which treatment of a composition containing dairy proteins that include whey proteins with a proteolytic enzyme occurs prior to any heating step, and in which the treatment is of short duration. The process includes incubating a dairy mixture containing the dairy proteins at a temperature and for a period of time that are sufficient to partially hydrolyze the proteins. The invention additionally provides an enzyme-modified cheese including partially proteolyzed dairy proteins wherein the partially proteolyzed dairy proteins contain partially proteolyzed whey proteins. The enzyme-modified cheese originates from any of a broad range of dairy liquids that contain dairy proteins. In important embodiments, the enzyme-modified cheese is made by the process of the invention.

10 Claims, 1 Drawing Sheet

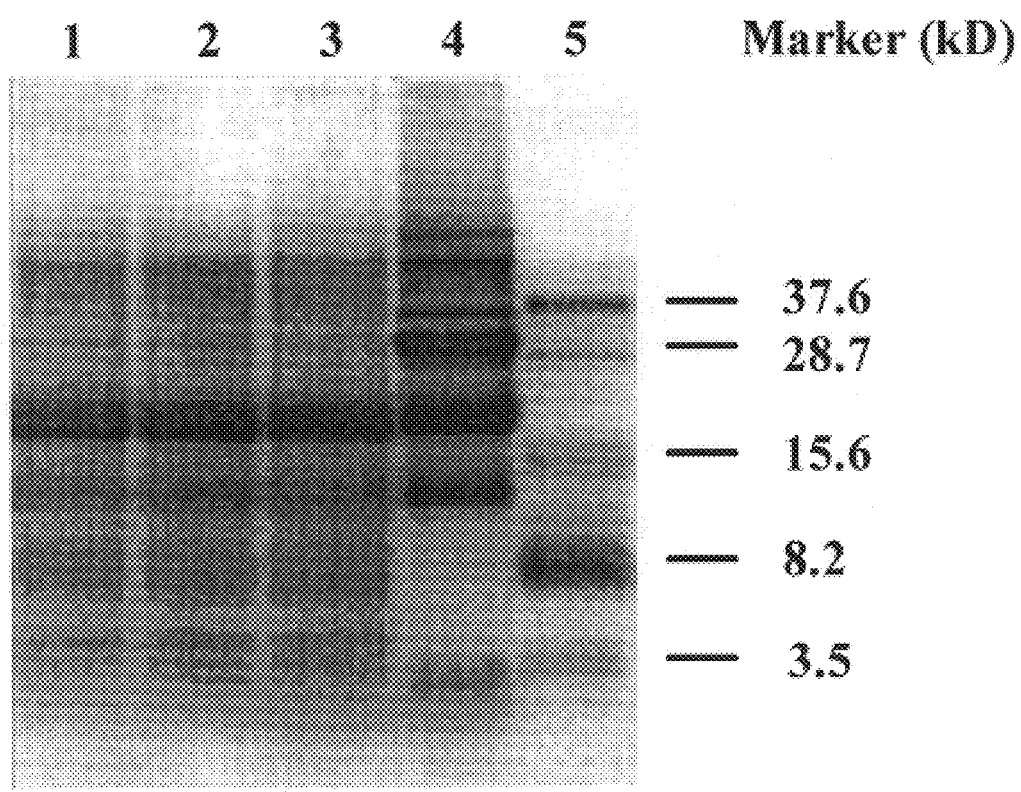
Figure

METHOD FOR PRODUCING ENZYME-MODIFIED CHEESE FLAVORINGS

FIELD OF THE INVENTION

This invention relates to a new and improved process for preparing enzyme-modified cheese flavorings, and to the enzyme-modified cheese flavorings resulting therefrom. This new process yields greater efficiency in producing enzyme-modified cheese flavorings, particularly from starting materials based on whey proteins.

BACKGROUND OF THE INVENTION

Enzyme modification of cheeses provides cheeses or cheese products with altered physical properties, such as melting and texture, and enhanced flavors. In general, enzyme modification may be carried out with hydrolytic enzymes that convert many of the components present in cheese. Most commonly, the enzymes used are lipases and/or proteases.

Many processes are known that employ both lipases and proteases. When applied to an already-prepared cheese curd, the product acquires new or enhanced flavors, and may be used either by itself or as a flavorant for other products. U.S. Pat. No. 4,595,594 discloses an intensified cheese flavor product that is prepared by incubating cheese, or cheese curd, with a lipase preferably in combination with a neutral protease. The enzyme(s) are allowed to partially digest the cheese as evidenced by a smooth, easily agitatable mixture, adding cream and incubating until the desired intensified cheese flavor is obtained. The intensity of the cheese flavor is so high that the product must be diluted prior to use. More specifically, Cheddar cheese or fresh curds are treated with the enzymes for about 48 hours.

U.S. Pat. No. 4,752,483 discloses a process for the rapid production of highly flavored cheese ingredients. A cheese curd is combined with water, protease, and lipase, and incubating for a time sufficient to produce a cheese-flavored ingredient. In particular, the process may use cheddar-type or American-type cheese curd less than about 60 days old. American-type cheese curd aged less than 60 days was reduced to particles less than about 2 millimeters. It was combined with aqueous lipase and protease and treated for 5.5 days to provide a highly flavored cheese ingredient. U.S. Pat. No. 5,211,972 discloses compositions including cheese or heavy cream in which the lipids or the proteins are enzymatically modified, and that provide a variety of desired cheese flavor profiles, without using exogenous microorganisms. Heavy cream and/or a hard, ripened cheese are treated with a lipolytic enzyme; hard, ripened cheese is treated with a proteolytic enzyme which is either an acid protease or a neutral protease. The lipolysis of the heavy cream proceeds at 38° C. for 16 hours, and the proteolysis of cheddar cheese likewise proceeds at 38° C. for 16 hours.

U.S. Pat. No. 5,455,051 discloses a flavorant composition having intensified blue cheese character which is obtained by treating blue cheese in an aqueous dispersion and incubated with spores of *Penicillium roquefortii* and with lipase and protease enzymes. The treatment proceeds long enough for the spores and the enzymes to hydrolyze and metabolize the blue cheese. In the examples, lipase and protease treatment, together with the spores, proceeds for about 24 hours.

Normally, enzyme-modified cheese flavorings are made using cheese or cheese curd as the starting material. These materials typically contain caseins as the principal protein and have low amounts of whey proteins, or none at all. It is less economical to make enzyme-modified cheese flavorings from cheese, as opposed to making them from milk or other dairy liquids. However, such dairy liquids contain whey proteins as well as, or in place of caseins. In processes in which milk or a milk product are used, they typically are subjected to a heating for pasteurization before being treated with the enzymes, in order to avoid microbial contamination during the lengthy enzyme treatment. Such heating has been found to be generally detrimental because, among other effects, it induces the whey proteins to aggregate. The aggregated whey proteins are not readily available for the action of an added protease. This difficulty is commonly overcome, when enzyme-modified cheese flavorings are prepared, by allowing incubation of the pasteurized milk or milk product for long periods (e.g., 64 hours or longer).

There remains a need, therefore, for a more efficient method of making enzyme-modified cheese flavorings that treats milk or a dairy liquid rather than treating a cheese curd or an aged, prepared cheese. There further remains a need for a method for melting enzyme-modified cheese flavorings which employs dairy liquids that include whey protein as the starting material and avoids coagulating aggregating the whey protein prior to being treated with the enzyme. In addition, there remains a need for a method of treating milk or a dairy liquid with enzyme for only a short period of time to produce an enzyme-modified cheese flavor, thereby increasing manufacturing efficiency The present invention addresses these needs.

SUMMARY OF THE INVENTION

The present invention provides an improved process for making enzyme-modified cheese flavorings in which treatment with a proteolytic enzyme occurs prior to any heating step, and in which the enzyme treatment is of relatively short duration (i.e., normally less than about 12 hours). The process includes the steps of:

(i) contacting a dairy liquid containing whey protein with a proteolytic enzyme to provide a dairy reaction mixture;

(ii) incubating the dairy reaction mixture at a temperature and for a period of time that are sufficient to partially hydrolyze the proteins;

(iii) pasteurizing the partially hydrolyzed dairy reaction mixture;

(iv) contacting the pasteurized mixture with a composition comprising a lipase and a cheese culture and incubating for a time and at a temperature that are sufficient for cheese flavor to develop; and (v) treating the fermented mixture with heat sufficient to inactivate the culture, destroy microbial contaminants, and inactivate the enzymes;

thereby providing the enzyme-modified cheese flavorings. The dairy liquid is chosen from among whole milk, reduced fat milk, fat-free milk, skim milk, milk protein concentrate, whey, whey protein isolate, whey protein concentrate, reconstituted milk solids, reconstituted whey solids, cream, and mixtures thereof.

In important embodiments, the proteolytic enzyme is chosen from among a bacterial protease such as the neutral protease from *Bacillus subtilis*, a protease derived from plant origins, a fungal protease, a fungal peptidase, a microbial protease, a microbial peptidases, a mammalian protease, and mixtures thereof. In other important embodiments, the dairy reaction mixture is incubated at a temperature between about 4° C. and about 70° C., and preferably, at a temperature between about 45° C. and about 55° C. In other significant embodiments, the dairy reaction mixture is incubated for a period of time between about 30 minutes and about 12 hours, and preferably, for a period of about 3 hours to about 5 hours. In an additional important embodiment, the composition that contacts the pasteurized mixture further includes a protease and/or a peptidase.

The invention additionally provides an enzyme-modified cheese flavoring containing partially proteolyzed dairy proteins, including partially proteolyzed whey proteins. Importantly, the partially proteolyzed dairy proteins include proteolysis products that have apparent molecular weights, as visualized by SDS-PAGE, of less than about 10 kDa, and even more importantly, less than about 3 kDa. The enzyme-modified cheese flavorings originate from any of a broad range of dairy liquids that contain dairy proteins. In important embodiments, the enzyme-modified cheese flavorings are made by the process of the invention described in the preceding paragraphs.

BRIEF DESCRIPTION OF THE DRAWING

The FIGURE illustrates the tricine SDS-PAGE of results obtained in Example 1. Lane 1, Sample 1 (dairy liquid, proteolysis for 4 hours); Lane 2, sample 2 (dairy liquid with added butter, proteolysis for 4 hours); Lane 3, Sample 3 (pasteurized dairy liquid, proteolysis for 63 hours); Lane 4, Control sample (dairy liquid plus proteolytic enzyme without proteolysis); Lane 5, molecular weight standards.

DETAILED DESCRIPTION OF THE INVENTION

The enzyme-modified cheese flavorings of the invention are compositions, derived from dairy liquids that include whey or whey proteins, having strong, intense, or enhanced flavors associated with any of a wide variety of cheeses. The present invention provides a novel and improved process for preparing enzyme-modified cheese flavorings, and the cheese flavorings obtained thereby, which optimizes the conditions employed in the proteolytic digestion. Without wishing to be limited by theory, it is believed that when a dairy liquid containing whey protein is pasteurized, the whey protein aggregates and/or coagulates. Such aggregates, if subjected to the action of a proteolytic enzyme, are digested very slowly in view of the aggregation. According to the present invention, aggregation of whey proteins before proteolysis is avoided by subjecting the dairy liquid to the action of the protease prior to any heat treatment. This improvement has the beneficial consequence that time and expenses are minimized; for example, there is no need for use of "sterile" water in preparing the proteolysis mixture since the composition will be pasteurized at a later step. Additional advantages include (1) use of a higher concentration of protein in preparing the dairy-enzyme mixture; (2) culture nutrients at the fermentation stage remain more available for the cheese flavoring to develop since the deactivation of vitamins and other nutrients which would occur during pasteurization will not have taken place; (3) hydrolyzed peptides are better nutrients for the microorganisms than intact proteins; and (4) a product is obtained that is more stable to microbial contamination, because the time allowed for proteolytic activity also permits microbial spores to mature so that a heat-susceptible form of the microorganism undergo the pasteurization steps.

As used herein, "whey protein" relates to the proteins contained in a dairy liquid obtained as a supernatant of the curds when milk or a product containing milk components are curded to produce a semisolid cheese curd. Whey protein is generally understood to include principally the globular proteins β-actoglobulin and α-lactalbumin; it also includes a significantly lower concentration of immunoglobulin and other globulins. The whey employed in the invention may be natural whey liquid directly provided by a cheese-making process. It may additionally be a whey concentrate obtained by processes known to the skilled artisan in dairy chemistry such as ultrafiltration (alone or combined with diafiltration). The whey may also be a reconstituted liquid obtained by adding water or an aqueous composition to whey solids, wherein the reconstituted concentration may be lower than, about equal to, or greater than the concentration of natural whey. All these whey preparations include whey protein.

In the present invention, whey protein may be prepared by treating whey to lower the concentration of, or eliminate, low molecular weight components of whey, such as lactose, by methods known in the dairy arts, including ultrafiltration (with or without diafiltration). In general, therefore, preparations of whey protein that may be used in the present invention contain whey protein, either alone or together with other components of whey, and at a broad range of concentrations.

As used herein, the term "dairy liquid" relates to milk, or to a milk product obtained by fractionation of raw milk to provide a liquid fraction, or a solid milk fraction that is reconstituted to a liquid. An important requirement for the dairy liquid used in the present invention is that it contains, at a minimum, whey protein as described above. Additionally, a dairy liquid employed in the present invention may include casein, occurring, for example, in the form of aggregates, or micelles, such that the dairy liquid coagulates to a cheese curd when subjected to a curding procedure. The milk may be treated to remove some, or all, of the butterfat, providing reduced fat milk, or fat-free milk, respectively. Furthermore, whole milk, reduced fat milk, skim milk, or fat-free milk may be concentrated by methods such as evaporation, ultrafiltration, ultrafiltration combined with diafiltration, and the like. Evaporation provides dairy compositions containing a higher concentration of all the nonvolatile components; ultrafiltration provides dairy liquids as the retentate having a higher concentration of the components that do not permeate the ultrafiltration membrane as compared to the starting liquid. In any case, the dairy proteins (including whey protein and any casein that may be present) are included among the retained solids, such that their concentrations in the resulting liquids are increased. Furthermore any of the above dairy liquids may be evaporated to dryness, providing milk solids originating from whole milk, reduced fat milk, skim milk, or fat-free milk. Any of these solids may be reconstituted by the addition of water or a suitable aqueous composition including milk or a milk fraction. Reconstitution of dry milk products thus provides dairy liquids that in general may have a broad range of final concentrations of proteins, butterfat, and other components. Additionally a dairy liquid as used herein may include added cream or other sources of butterfat. All the above liquids are included in the designation of "dairy liquids" as used herein.

The dairy liquids employed in the present invention may originate from any lactating livestock animal whose milk is useful as a source of human food. Such livestock animals include, by way of nonlimiting example, cows, buffalo, other ruminants, goats, sheep, and the like. In a preferred embodiment, cows' milk provides the dairy liquid used in the practice of the invention.

As used herein, "a composition comprising dairy proteins" relates to a dairy liquid, or to at least one dry preparation containing dairy proteins such as dry milk, or dry whey, or whey protein powder, which has been hydrated by the addition of at least small amount of a water-containing or aqueous composition. Dairy proteins include, by way of non-limiting example, caseins and whey proteins.

As used herein, a "proteolytic enzyme" or a "protease" is a proteolytic enzyme which has the activity of hydrolyzing internal peptide bonds of proteins, but is not a rennet, where rennet is a generic term used in the fields of dairy science and cheese making to designate an activity obtained from the lining of the stomachs of immature mammals that consume maternal milk. Rennet is also known as chymosin. Thus, a proteolytic enzyme or protease employed in the present invention relates to an enzyme which partially digests the proteins of dairy liquids, including, for example, whey proteins and caseins, but does not exhibit the proteolytic specificity of a rennet.

Among the proteases that may be used in the present invention are the neutral protease obtained from *Bacillus sublilis* (Neutrase™, Novo Nordisk); a protease derived from plant origins such as bromelain, papain or actinidain; a fungal protease such as those originating from *Aspergillus niger* or *Aspergillus oryzae*, for example the product termed fungal protease concentrate provided by Genencor; Flavozyme™ (Novo Nordisk), which contains a mixture of fungal proteases and peptidases; Promod 215™ (Biocatalysts Ltd., Mid Glamorgan, UK) which is a mixture of microbial proteases and peptidases; and mammalian proteases including, by way of nonlimiting example, pepsin or serine proteases including trypsin and chymotrypsin; and mixtures thereof.

As used herein, the term "partial proteolysis" of dairy proteins, and, in particular, "partial proteolysis" of whey proteins, and the corresponding descriptive term "partially proteolyzed" with reference to a dairy protein, relate to proteolytic digestion of the dairy protein, including at least the whey protein, using a non-rennet protease. "Partial proteolysis" relates to endopeptidase activity directed against the proteins such that only a fraction of the total number peptide bonds is hydrolyzed. By way of non-limiting example, and for purposes of indicating the general phenomenon, peptides of apparent molecular weights of at least about 1,000 Da, or about 2,000 Da, or about 10 kDa, or higher, may be detected upon completing the proteolysis.

In significant embodiments of the invention, the partial proteolytic digestion of the proteins of the dairy liquid is optimized by keeping the concentration of both the protein and the enzyme high. Thus, as an example, dry milk proteins and the proteolytic enzyme are suspended in a relatively small amount of water to form a paste which is termed herein a "dairy reaction mixture". Alternatively a dairy liquid having a high concentration of dairy proteins may be blended with dry proteolytic enzyme, or with a concentrated suspension of a proteolytic enzyme in an aqueous composition to form the dairy reaction mixture.

The dairy reaction mixture is incubated at a temperature and for a period of time that are sufficient to partially hydrolyze the proteins of the dairy liquid. For example, the dairy mixture may be incubated at a temperature between about 4° C. and about 70° C., and preferably, at a temperature between about 45° C. and about 52° C. Additionally, the dairy mixture is incubated for a period of time between about 30 minutes and about 12 hours; preferably it is incubated for a period of about 3 hours to about 5 hours. Partial hydrolysis of the proteins in the dairy mixture is undertaken in order to provide melting, textural and organoleptic properties to the resulting cheese flavoring that are considered favorable by the consuming public. The hydrolysis may be followed by tracing the loss of starting proteins, and/or the appearance of proteolytic digestion products using, for example, analytical methods such as SDS- PAGE, capillary electrophoresis, and various forms of liquid chromatography. For example, partial proteolysis of any of the dairy proteins in the starting dairy liquid may provide peptide products that have apparent molecular weights, as visualized by SDS- PAGE, at least about 1,000 Da, or about 2,000 Da, or about 10 kDa, or higher, up to the apparent molecular weight, of the corresponding unproteolyzed dairy protein from which the peptides are derived.

After proteolysis, the dairy mixture is heated sufficiently to pasteurize the mixture. The heat-treated dairy mixture, containing partial hydrolytic breakdown products of the dairy proteins, is then treated with a lipase and a particular cheese culture, and optionally with additional proteases and/or peptidases, to prepare a product having a known, intended, and characteristic cheese flavor. In particular, the pasteurized dairy mixture is contacted with a composition containing a lipase and a cheese culture and incubating for a time sufficient for the desired cheese flavor to develop. The resulting culture is treated with heat sufficient to inactivate the culture, destroy microbial contaminants, and inactivate the enzymes. Generally, a temperature of about 65 to about 95° C. for about 15 to about 60 minutes is sufficient. The product provides the enzyme-modified cheese flavoring.

The following examples are intended to illustrate the invention and not to limit it. Unless otherwise indicated, all percentages are by weight.

EXAMPLE 1

Enzame-modified Cheese Flavorings and Their Analysis

Various enzymes and experimental conditions used in the preparation of enzyme-modified cheese flavorings were assessed. Six samples (including one control) were prepared using the conditions as detailed in Table 1. For all samples, 0.70 lb of milk protein concentrate (MPC 1100, New Zealand Milk Products, Chicago, Ill.), 1.42 lb of Krafen™ (spray dried sweet whey, Kraft Foods, Glenview, Ill.), and 1.14 lb of whey protein (Mgelei 90-2, Melei AG, Munich, Germany) were blended with 5.20 lb of warm water (50° C.) to prepare a dairy liquid. Melted butter (61.2 g) was added to 338.8 g of the dairy liquid in samples 2 and 3. The control and sample 3 were pasteurized by heating to 72° C. for 30 min. A protease (3444 units of Neutrasem™ (Novo Nordisk, Franklin, Ky.), 1725 units of Flavozyme™ (Novo Nordisk), or 5368 units of Umamizyme™ (Amano Ltd., Tokyo, Japan)) was then added to samples 1–5 as shown in Table 1. A unit is defined as the amount of enzyme that liberates the equivalent of one micromole of tyrosine per minute on 0.5% casein substrate at 37° C. in 0.1 M Tris-HCI buffer, pH 7.5. In Table 1, the enzyme labeled "A" is Neutrase™; the enzyme labeled "B" is Flavozyme™; and the enzyme labeled "C" is Umamizyme™. Samples 1–5 were incubated at 50° C. for 4 hours. Samples 1, 2, 4, and 5 were pasteurized at 72° C. for 30 min. Then all samples were treated with 1.1 g of lipase (pregastric lipase from calf or kid (SKW Biosystems, Waukesha, Wis.), 0.62 g of Enzobact™ (dried, attenuated culture of *Lactobacillus helvelicus*, Medipharm AB, Kagerod, Sweden), and 0.2 g of LC-20 culture (direct vat set culture of *Lactobacillus casei*; Marshall Laboratories, Milwaukee, Wis.). All samples were cultured at 40° C. for 59 hours (such that sample 3 was incubated for a total of 63 hours at the two temperatures). They were heat inactivated at 85° C. for 30 min, cooled and stored in a refrigerator.

Table 1 provides a summary of the conditions employed for each sample. The rows describe sequential additions or operations. A plus sign ("+") indicates that either the component was added or the process step was carried out; and a negative sign ("−") indicates that the component was not added or the process step was not carried out. For example, in Sample 1, butter was added after enzyme treatment; in contrast, for Sample 2, butter was added before the enzyme treatment.

TABLE 1

Samples of enzyme-modified daily liquids.

|  | Control | 1 | 2 | 3 | 4 | 5 |
| --- | --- | --- | --- | --- | --- | --- |
| Protein | + | + | + | + | + | + |
| Butter | − | − | + | + | − | − |
| Pasteurize | + | − | − | + | − | − |
| Enzyme | − | A | A | A | B | C |
| Temp (° C.)/ Time (hr) | − | 50/4 | 50/4 | 50/4 | 50/4 | 50/4 |
| Butter | − | + | − | − | − | − |
| Pasteurize | − | + | + | − | + | + |
| Lipase & culture | + | + | + | + | + | + |
| Pasteurize | + | + | + | + | + | + |

FIG. 1 shows SDS-PAGE results for the control (in Lane 4) and for samples 1–3 in Lanes 1–3, respectively. Lane 5 shows molecular weight markers. The experimental samples indicate no perceptible difference between the digestions conducted for 4 hours under conditions of the process of the invention (Lanes 1 and 2) and the proteolysis conducted for 63 hours after pasteurization, as is done in conventional practice (Lane 3). Thus, the process of the present invention surprisingly offers the advantage of achieving results comparable to those attained using methods applied in the art, but in much shorter times than employed in the art. It is also observed that samples 1 and 2 are essentially identical, suggesting that inclusion or omission of a lipid such as butter has no perceptible effect on the proteolytic digestion. Similar results are obtained with other proteases (not shown).

Neutrase™ is less reactive toward whey protein than are other proteases. As a result, more bands for protein fragments are visible on the gel after proteolysis by Neutrase™ than for other proteases. This is advantageous for the process of the invention, for the subsequent steps leading to the production of cheese can be pursued without difficulty. Other proteases, such as Umamizyme™ (sample 5), for example, are so reactive that the sample was essentially liquefied within 30 min of hydrolysis.

The various proteases employed (see Table 1) lead to widely differing results, as shown by chemical analysis and observation of the texture of the final enzyme-modified cheese flavorings (see Table 2). In Table 2, the row captioned TNBS provides a measure of the amino groups produced as a result of proteolysis; TNBS, trinitrobenzenesulfonic acid, reacts with amino groups to provide a colored product which can be detected. An OD (450 nm) value of 0.12 for TNBS corresponds to approximately 10 micromoles of leucine.

TABLE 2

Comparison of effects of various proteases on enzyme-modified cheese.

|  | Control | 1 | 2 | 3 | 4 | 5 |
| --- | --- | --- | --- | --- | --- | --- |
| Proteolysis (hr) | 0 | 4 | 4 | 63 | 4 | 4 |
| Product pH | 4.42 | 4.42 | 4.39 | 4.45 | 4.83 | 4.56 |
| Titratable Acidity (%) | 2.61 | 3.14 | 3.11 | 3.38 | 2.92 | 3.92 |
| TNBS (OD at 450 nm) | 0.060 | 0.152 | 0.155 | 0.159 | 0.301 | 0.537 |
| Product texture | firm paste | suspension | suspension | paste | suspension | liquid |

The results in Table 2 show that the choice of protease can affect the properties of the final product to a significant extent. The control maintains the paste consistency of the starting dairy liquid. The experimental samples using Neutrase™ (samples 1 and 2) provide a moderate degree of hydrolysis of the protein, as seen by the titratable acidity and TNBS results. The cheese product is a suspension in both samples. Comparison of samples 1 and 2 suggests that the presence of lipid, arising from the addition of butter, during proteolysis has no significant effect on the rate of proteolysis. Therefore, the addition of lipid or fat can be made before or after the proteolysis step. The Neutrase™ control, sample 3, in which heat treatment occurs prior to exposure to the enzyme, retains the paste-like consistency of the control, even though the titratable acidity and TNBS results do not differ significantly (titratable acidity is about 8% higher) from those of the experimental samples. Since the protease is not inactivated in sample 3, it is possible that proteolysis continues during the fermentation incubation.

Treatment with Flavozymem™ (sample 4) results in a higher degree of hydrolysis as measured by TNBS while providing a moderate level of titratable acidity. The cheese product is a suspension. Use of Umamizymem™ (sample 5), in contrast to the other enzymes, yields a liquified product as a result of a high level of proteolytic activity. The high extent of proteolysis is evident from the exceptionally high values of the TNBS reading and the titratable acidity.

Organoleptic evaluation of these samples indicated no significant differences in their flavors and tastes.

EXAMPLE 2

Enzyme-modified Cheese Preparations and Analysis Using Different Proteases.

Two proteases different from those used in Example 1, namely, Promod™ (Biocatalysts Ltd., Mid Glamorgan, UK), and bromelain (Valley Research, Inc., Hammond, Ind.), as well as Umamizmem™, and various experimental conditions were used in the preparation of enzyme-modified cheese, and the products were assessed. Seven samples were prepared (Table 3). For all samples 0.70 lb of milk protein concentrate (MPC 1100), 1.42 lb of Krafen™, and 1.14 lb of whey protein (Melei 90–2) were blended with 5.20 lb of warm water (60° C.) to prepare a dairy liquid. Melted butter (76.5 g) was added to 423.5 g of the dairy liquid in samples 2 and 3. The control and samples 3 and 5 were pasteurized by heating to 72° C. for 30 min. A protease was added to samples 1–6 as shown. Samples 1, 2, 4, and 6 were incubated at 53° C. for 4.0 hours. All samples were pasteurized at 72° C. for 30 min. Sample 3 then received Promod™, and sample 5 received bromelain. Then all samples were treated with 1.35 g of lipase, 0.8 g of Enzobact™, and 0.25 g of LC-20 culture. All samples were cultured at 40° C. for 48 hours, then heat inactivated at 85° C. for 30 min, cooled and stored in a refrigerator.

The same conventions are used in Table 3 as described above for Table 1. In Table 3, the enzyme labeled "C" is Umamizyme™ (1035 units were added); the enzyme labeled "D" is Promod™ (1147 units were added); and the enzyme labeled "E" is bromelain (972 units were added).

TABLE 3

Samples of enzyme-modified dairy liquids.

|  | Control | 1 | 2 | 3 | 4 | 5 | 6 |
|---|---|---|---|---|---|---|---|
| Protein | + | + | + | + | + | + | + |
| Butter | – | – | + | + | – | + | – |
| Pasteurize | + | – | – | + | – | + | – |
| Enzyme | – | D | D | – | E | – | C |
| Temp (° C.)/ Time (hr). | – | 50/4 | 50/4 | – | 50/4 | – | 50/4 |
| Butter | – | + | – | – | – | – | – |
| Pasteurize | – | + | + | – | + | – | + |
| Enzyme | – | – | – | D | – | E | – |
| Lipase & culture | + | + | + | + | + | + | + |
| Pasteurize | + | + | + | + | + | + | + |

The results of chemical analysis of the final products obtained from this experiment are presented in Table 4. "ND" in the table indicates that the parameter was not determined. It is seen that the different enzymes employed provide different levels of proteolysis, as determined by the TNBS value. Longer digestion times (samples 3 and 5) lead to higher levels of proteolysis than the short times used with samples 1, 2, and 4.

TABLE 4

Chemical Analysis of Final Products

|  | Control | 1 | 2 | 3 | 4 | 5 | 6 |
|---|---|---|---|---|---|---|---|
| Proteolysis (hr) | 0 | 4 | 4 | 48 | 4 | 48 | 4 |
| Product pH | 4.91 | 4.69 | ND | 4.40 | 4.60 | 4.53 | 4.50 |
| Titratable Acidity (%) | 2.10 | 3.66 | 3.64 | 4.27 | 3.06 | 3.57 | 3.39 |
| TNBS (OD at 450 nm) | 0.063 | 0.281 | ND | 0.399 | 0.187 | 0.213 | 0.314 |

We claim:

1. A process for making an enzyme-modified cheese flavoring comprising the steps of:

(i) contacting a dairy liquid containing whey proteins with a proteolytic enzyme to provide a dairy reaction mixture, wherein the diary liquid is not subjected to heat treatment prior to contact with the proteolytic enzyme;

(ii) incubating the dairy reaction mixture at a temperature and for a period of time that are sufficient to partially proteolyze the proteins, wherein the period of time is less than about 12 hours;

(iii) pasteurizing the partially proteolyzed dairy reaction mixture;

(iv) contacting the pasteurized mixture with a composition comprising a lipase and a cheese culture and incubating for a time and at a temperature that are sufficient for cheese flavor to develop; and (v) treating the fermented mixture with heat sufficient to inactivate the cheese culture, destroy microbial contaminants, and inactivate the lipase;

thereby providing the enzyme-modified cheese flavoring.

2. The process described in claim 1, wherein the dairy liquid is chosen from the group consisting of whole milk, reduced fat milk, fat-free milk, skim milk, milk protein concentrate, whey, whey protein isolate, whey protein concentrate, reconstituted milk solids, reconstituted whey solids, cream, and mixtures thereof.

3. The process described in claim 1, wherein the proteolytic enzyme is chosen from the group consisting of a bacterial protease, a protease derived from plant origins, a fungal protease, a fungal peptidase, a microbial protease, a microbial peptidase, a mammalian protease, and mixtures thereof.

4. The process described in claim 1, wherein the dairy reaction mixture in step (ii) is incubated at a temperature between about 4° C. and about 70° C.

5. The process described in claim 4, wherein the dairy reaction mixture is incubated at a temperature between about 45° C. and about 55° C.

6. The process described in claim 1, wherein the dairy reaction mixture in step (ii) is incubated for a period of time between about 30 minutes and about 12 hours.

7. The process described in claim 6, wherein the dairy reaction mixture is incubated for a period of about 3 hours to about 5 hours.

8. The process described in claim 1, wherein the composition that contacts the pasteurized mixture in step (iv) further includes a protease, a peptidase, or mixtures thereof.

9. The process described in claim 1, wherein the dairy liquid is chosen from the group consisting of whey, whey protein isolate, whey protein concentrate, reconstituted whey solids, and mixtures thereof, and wherein the enzyme-modified cheese flavoring comprises partially proteolized whey proteins having apparent molecules weights, as visualized by SDS-Page, of less than about 10 kDa.

10. The process as described in claim 9, when the apparent molecules weights are less than about 3 kDa.

* * * * *